United States Patent [19]

Hattori et al.

[11] Patent Number: 5,254,705

[45] Date of Patent: Oct. 19, 1993

[54] PROCESS FOR PRODUCING DESULFURIZED FATS AND OILS OR FATTY ACID ESTERS AND PROCESS FOR PRODUCING ALCOHOLS BY USING SAID DESULFURIZED FATS AND OILS OR FATTY ACID ESTERS

[75] Inventors: Yasuyuki Hattori; Hiroyuki Tamura; Hidetoshi Kadowaki; Kiyoshi Tsukada, all of Wakayama, Japan

[73] Assignee: Kao Corporation, Tokyo, Japan

[21] Appl. No.: 890,109

[22] Filed: May 29, 1992

[30] Foreign Application Priority Data

May 31, 1991 [JP] Japan ................................. 3-129234
Sep. 25, 1991 [JP] Japan ................................. 3-245683

[51] Int. Cl.$^5$ ............................................ C07C 51/36
[52] U.S. Cl. ...................................... 554/141; 554/147; 554/175; 568/885; 502/331; 502/33
[58] Field of Search ................. 554/141, 147, 175; 568/885; 202/318, 331

[56] References Cited

U.S. PATENT DOCUMENTS 4,918,248  4/1990  Hattori et al. .................... 568/885
5,120,885  6/1992  Tsukada et al. ................... 568/885

OTHER PUBLICATIONS

Tyutyunnikav et al, Chemical Abstracts, vol. 82, #24, 1973, 160729r.
World Patents Index Latest Section Ch, Week 8251, Derwent Publications Ltd., Class D, AN 82-09936J.
World Patents Index Latest Section Ch, Week 8642, Derwent Publications Ltd., Class D, AN 86-277892.
World Patents Index Latest Section Ch, Week 7108, Derwent Publications Ltd., Class D, AN 71-15004S.
Chemical Abstracts, vol. 95, No. 03, Aug. 1981, abstract No. 45104Q.

*Primary Examiner*—José G. Dees
*Assistant Examiner*—D. Carr
*Attorney, Agent, or Firm*—Sughrue, Mion, Zinn, Macpeak & Seas

[57] ABSTRACT

A process for producing desulfurized fats and oils or fatty acid esters, which are highly suitable as a starting material for producing alcohols via hydrogenation, at a high yield is disclosed. Desulfurized fats and oils or fatty acid esters are obtained by contacting fats and oils or fatty acid esters with a catalyst represented by the following formula (I) under a hydrogen atmosphere or a mixture of hydrogen with an inert gas:

$$Ni.Cu_xO_y \qquad (I)$$

wherein x represents an atomic ratio of Cu determined by referring Ni as 1 and a value of from 0.02 to 8; and y is an atomic ratio of oxygen satisfying the valence requirements of Ni and Cu. A process for producing alcohols using the desulfurized fats and oils or fatty acid esters is also disclosed. A process for producing an alcohols using desulfurized fats and oils or fatty acid esters is also disclosed. According to the process for producing an alcohol of the present invention, an alcohol of a high purity and good qualities can efficiently and effectively be produced.

4 Claims, No Drawings

PROCESS FOR PRODUCING DESULFURIZED FATS AND OILS OR FATTY ACID ESTERS AND PROCESS FOR PRODUCING ALCOHOLS BY USING SAID DESULFURIZED FATS AND OILS OR FATTY ACID ESTERS

FIELD OF THE INVENTION

This invention relates to a process for producing desulfurized fats and oils or fatty acid esters and a process for producing alcohols by using the desulfurized fats and oils or fatty acid esters.

More particularly, it relates to a process for producing desulfurized fats and oils or fatty acid esters by catalytically hydrogenating various fats and oils or fatty acid esters to thereby give the corresponding hydrogenated fatty acids, aliphatic alcohols or aliphatic amines, wherein the starting materials is preliminarily treated with a specific catalyst containing copper to thereby reduce a content of sulfur which acts as a catalyst poison. The present invention further relates to a process for producing alcohols by catalytically reducing fats and oils or fatty acid esters with hydrogen in the presence of a catalyst for ester reduction, wherein the aforesaid desulfurized fats and oils or fatty acid esters are used to thereby extend the catalyst life of said catalyst for ester reduction.

BACKGROUND OF THE INVENTION

Fat and oils (the term "fats and oils" as used herein means triglycerides) and fatty acid esters derived therefrom (the term "fatty acid esters" as used herein means esters of fatty acids with lower or higher alcohols other than triglycerides) usually contain at least several to several tens ppm of sulfur. In the production of alcohols starting from these fats and oils or fatty acid esters (i.e., "starting oil" or "starting ester") in the presence of an ester reduction catalyst, sulfur compounds contained in a trace amount in the starting oils would act as catalyst poisons and thus considerably shorten the activity life of the ester reduction catalyst.

Thus, the present inventors have examined various refining processes for reducing the sulfur contents of fats or fatty acid esters to be used as a starting material for producing alcohols. As a result, they have clarified the following problems.

(1) Problems in purification by distillation:

When fatty acid methyl esters derived from natural fats and oils in a conventional manner are distilled, the sulfur content is reduced to 10% and 20%, based on the initial content, respectively at distillation yields of 90% and 98%. In order to reduce the sulfur content of commonly available fatty acid methyl esters to a desired level, however, a distillation loss of 5% or greater is unavoidable. In this case, further, the alkyl distribution in the material is considerably changed.

In the case of fats and oils or esters fatty acids with higher alcohols having a higher boiling point, it is practically difficult to eliminate sulfur compounds contained therein by distillation.

(2) Problems in purification with the use of desulfurization catalysts:

In the field of petroleum refining, molybdenum or tungsten catalysts have been employed for eliminating sulfur compounds contained in gas oil or oil fuel as described, for example, in *Shokubai Process Kagcaku* (*Chemistry of Catalytic Process*), published by Tokyo Kagaku Dojin.

However it is required to heat these catalysts to 300° C. or above in order to achieve the desulfurized activity. When fats and oils or fatty acid esters are hydrogenated at such a high temperature, the hydrogenolysis of ester groups results in an increase in an acid value (AV) and accelerates the decomposition of materials.

(3) Problems in other purification procedures (treatment with adsorbents, steaming or alkali-treatment):

In these procedures, even though fully performed, from 3 to 5 ppm of sulfur would remain and, therefore, the desired fats or fatty acid esters of a sulfur content (sulfur content: 0.6 ppm or below) cannot be obtained thereby.

SUMMARY OF THE INVENTION

Under these circumstances, the present inventors have conducted extensive studies in order to reduce the sulfur content of fats and oils or fatty acid esters to a desired level. As a result, they have successfully found out that fats and oils or fatty acid esters highly suitable as a starting material for producing alcohols via hydrogenation can be produced at a high yield by treating fats and oils or fatty acid esters with the use of a specific nickel/copper catalyst under a hydrogen atmosphere or a mixture of hydrogen with an inert gas, thus completing the present invention.

Accordingly, the present invention provides a process for producing desulfurized fats and oils or fatty acid esters which comprises contacting fats and oils or fatty acid esters with a catalyst represented by the following formula (I) under a hydrogen atmosphere or a mixture of hydrogen with an inert gas:

$$Ni.Cu_xO_y \qquad (I)$$

wherein x represents an atomic ratio of Cu determined by referring Ni as 1 and a value of from 0.02 to 8; and y is an atomic ratio of oxygen satisfying the valence requirements of Ni and Cu.

The fatty acid ester to be used in the present invention may be distilled prior to the treatment in the presence of the above-mentioned specific nickel/copper catalyst under specific conditions.

The present invention further provides a process for producing alcohols which comprises the steps of:

(1) contacting fats and oils or fatty acid esters with a catalyst represented by the following formula (I) under a hydrogen atmosphere or a mixture of hydrogen and an inert gas:

$$Ni.Cu_xO_y \qquad (I)$$

wherein x represents an atomic ratio of Cu determined by referring Ni as 1 and a value of from 0.02 to 8; and y is an atomic ratio of oxygen satisfying the valence requirements of Ni and Cu; and (2) catalytically reducing the desulfurized fats and oils or fatty acid esters obtained in the step (1) with hydrogen in the presence of a catalyst for ester reduction.

DETAILED DESCRIPTION OF THE INVENTION

Now the present invention will be described in greater detail.

When fats and oils or fatty acid esters derived therefrom (the term "fatty acid ester" as used herein means an ester of an aliphatic carboxylic acid with a lower or higher alcohol) are catalytically reduced with hydrogen in the presence of an ester reduction catalyst so as to give the corresponding aliphatic alcohol, the qualities of the starting material largely affect the activity life of the catalyst. Thus, the present inventors have examined substances contaminating the starting oil which affect the activity life of the ester reduction catalyst. As a result, they have found out that free fatty acids cause serious catalyst poisoning, in addition to sulfur compounds and halides which have been already known as catalyst poisons. It has been widely known that sulfur compounds and halides act as catalyst poisons for hydrogenation catalysts. It is therefore preferable to minimize the contents of these catalyst poisons prior to the reaction. Since commonly available starting oils contains little halides, it is the most important to reduce the content of sulfur compounds. Ester reduction catalysts employed for industrial purposes are copper/chromium or copper/zinc catalysts which frequently suffer from corrosion with free fatty acids. It is therefore required to minimize the free acid concentration of staring oils.

In order to examine the acceptable concentrations of sulfur compounds and free fatty acids in starting oils, therefore, methyl esters derived from coconut oil or palm kernel oil in a conventional manner are treated with copper/chromium and copper/zinc catalyst. For comparison, methyl esters obtained by distilling the above-mentioned starting oil (distillation yield: 90%) which contain 0.3 to 0.4 ppm of sulfur and have an acid value (AV, KOH mg/g) of 0.1 or below are used. As a result, it is found out that a catalyst life almost comparable to the one achieved by using the distilled methyl esters can be obtained by using a starting material of a sulfur content of 0.6 ppm or less, preferably 0.3 ppm or less, and an acid value (AV) of 2 or below.

Accordingly, it is required that the desulfurized starting fats and oils or fatty acid esters contain 0.6 ppm or less, preferably 0.3 ppm or less, of sulfur and has an acid value (KOH mg/g) of 2 or below.

Desulfurization Process:

The catalyst to be used in the present invention is represented by the above formula (I) wherein the value of x ranges from 0.02 to 8, preferably from 0.02 to 2.0, and the value of y preferably ranges from 1.02 to 3.0. When the value of x is smaller than the lower limit as specified above, a large amount of fatty acids are formed as side products. On the other hand, the value of x exceeding the upper limit is disadvantageous from the viewpoint of desulfurization.

In the present invention, the catalyst represented by formula (I) is usually in the form of being carried on a carrier or a mixture with a carrier. As the carrier, well known ones (for example, a silica, an alumina, a silica/alumina, a zeolite, a diatomaceous earth, an active clay, a titanium, a zirconium, an activated carbon) as disclosed, for example, in Shokubai Chosei (Preparation of catalyst), published by Kodansha Scientific, pages 16–63 (1974) may be used. It is preferable that the ratio by weight of the catalyst of formula (I) to the carrier falls within the following range:

$$\frac{\text{Catalyst of formula (I)}}{\text{Carrier}} = 100/0 \text{ to } 10/90.$$

The ratio by weight of the catalyst of formula (I) to the carrier is preferably 80/20 to 20/80. When the amount of the carrier is excessively large, the content of active Ni is reduced and, as a result, the desired performance can hardly be achieved.

The above-mentioned catalyst may be produced by any method as disclosed, for example, in *Shokubai Chosei Kagaku* (Chemistry in Preparation of Catalyst), published by Kodansha Scientific, pages 13–56 (1980), without restriction. For example, it may be obtained by preparing a mixture by co-precipitation, impregnation or homogeneous kneading and then baking the resulting mixture. Alternately, any of these preparation methods may be combined with each other, if required.

The form of the catalyst may be appropriately selected from among powdery forms and molded forms depending on the system for treating the starting fats and oils or fatty acid esters. The catalyst is activated by reducing with hydrogen prior to the use. It is also possible, in some cases, that the catalyst is previously reduced and stabilized by a known method and then used either as such or after activating again by reducing.

The aforesaid desulfurization treatment may be effected continuously, semi-batchwise or batchwise. For mass treatment, a continuous reaction system is preferred. Continuous treatment can be carried out in any of many widely practiced reaction systems such as a fixed bed system, a moving bed system, a fluidized bed system or systems used, for example, in petroleum refining, e.g., catalytic desulfurization, catalytic cracking and catalytic reforming. In general, where the starting oils have a relatively low sulfur content, a fixed bed system in which a catalyst can be used in a high concentration is preferred. Where the starting oils have a high sulfur content, the treatment may be performed in a moving bed or fluidized bed system in which a spent catalyst having reduced activity can be exchanged continuously. It is preferable to select the fixed bed system so as to simplify the procedure.

Details of the fixed bed system which can be used in the present invention are described, for example, in *The Oil and Gas Journal*, May 1966, pages 173–178 (1066) and *Hydrocarbon Processing*, November, 1970, pages 187–191 (1970). Details of the fluidized bed system which can be used in the present invention are described, for example, in G. Diecklmann and H. J. Heinz, The Basics of Industrial *Oleochemistry*, published by Peter Promp GmbH., pages 91–102 (1988). Details of the moving bed system which can be used in the present invention are described, for example, in W. C. van Zijll Langhout et al., *The Oil and Gas Journal*, Dec., pages 120–126 (1980).

The fats and oils or fatty acid esters are to be treated in the presence of a catalyst represented by the above formula (I) under the conditions as specified below.

In the case of a continuous reaction system, for example, hydrogen or a mixture of hydrogen with an inert gas may be used as a treatment gas. When hydrogen is fed as a mixture with the inert gas, a volume ratio of hydrogen in the mixture may range from 4 to 100%. Examples of the inert gas include nitrogen, argon, helium and methane. The treatment pressure ranges from 0.1 to 500 kg/cm$^2$. It is still preferable, in this case, to control the treatment pressure to 1 to 300 kg/cm$^2$ so as to achieve a high desulfurizing activity and to suppress the decomposition of the starting oil. Under a hydrogen atmosphere, a larger amount of hydrogenation side products are formed as the desulfurization proceeds under a higher pressure. The treatment temperature may range from 30° to 250° C. It is preferable to perform the treatment at a temperature of from 50° to 250° C., since a lower temperature causes a decrease in the desulfurizing activity while a higher temperature under a hydrogen atmosphere elevates the amount of hydrogenation side products.

The starting fat or fatty acid ester may be preferably fed at a liquid hourly space velocity (LHSV, i.e., reaction tower volume ratio per hour) of from 0.1 to 5.0 $hr^{-1}$. A lower LHSV is disadvantageous from a viewpoint of productivity.

In a fixed bed continuous reaction system, the starting oil to be treated may be passed either in up-flow system, trickle-flow system or counter-flow system. When a large amount of a liquid or gas is to be flown, the counter-flow system is disadvantageous. On the other hand, the up-flow system is disadvantageous from the viewpoints of requiring a large catalyst strength and pressure loss in the flowing gas. Therefore, the trickle-flow system may be preferably employed.

According to the process disclosed in the present invention, the fats and oils or fatty acid esters of a sulfur content of 0.6 ppm or less and an acid value (AV) of 2 or below thus obtained are then catalytically reduced with hydrogen with the use of a copper ester reduction catalyst so as to converted into the corresponding alcohols. The term "copper ester reduction catalyst" means a catalyst comprising copper as the active component, for example, a conventionally known copper-chromium, copper-zinc, copper-iron-aluminum or copper-silica catalyst. The ester reduction may be performed either on a liquid phase suspension bed or on a fixed bed in the presence of the above-mentioned catalyst.

Examples of the fats and oils to be used in the present invention include animal and vegetable fats and oils such as coconut oil, palm oil, palm kernel oil, soybean oil, rapeseed oil, beef tallow, lard and fish oil as well as those obtained by hydrogenating the same.

Examples of the fatty acids constituting the fatty acid ester to be used in the present invention include caproic acid, caprylic acid, capric acid, lauric acid, myristic acid, palmitic acid, stearic acid, eicosanoic acid, docosanoic acid, oleic acid and erucic acid. Examples of the alcohol constituting the same include methanol, ethanol, 1-propanol, 2-propanol, 1-butanol, 2-butanol, 2-ethylhexanol, 2,2-dimethyl-1,3-propanediol, ethylene glycol, propylene glycol, 1,4-butanediol, 1,6-hexanediol, 1,10-decanediol, cyclohexanol, benzyl alcohol, diethylene glycol, glycerol and trimethylolpropane.

Process for Producing Alcohol by Catalytic Reduction:

The fats and oils or fatty acid esters of a sulfur content of 0.6 ppm or below, which have been obtained by the purification process of the present invention, can be then converted into the corresponding alcohols by catalytically reducing with hydrogen in the presence of a catalyst for ester reduction. As the catalyst for ester reduction to be used here, copper-based catalysts for ester reduction are preferable. For example, known catalyst systems such as copper-chromium, copper-zinc, copper-iron-aluminum and copper-silica may be cited. The ester reduction may be effected in the presence of the aforesaid catalyst either in a liquid phase suspended bed system or in a fixed bed system.

Conditions for the ester reduction may be selected in accordance with those commonly known in the art. When a liquid phase suspended bed system is employed, the catalyst is preferably used in an amount of from 0.1 to 20% by weight based on the starting fats and oils or fatty acid esters, though the catalyst amount may be optionally selected depending on the reaction temperature or the reaction pressure within a range yielding a reaction rate sufficient for practical production. The reaction temperature may range from 160° to 350° C., preferably from 200° to 280° C. The reaction pressure may range from 1 to 350 $kg/cm^2$, preferably from 30 to 300 $kg/cm^2$.

When a fixed bed system is employed, the catalyst is employed in a molded form such as column, pellet or spherical form. The reaction temperature may range from 130° to 300° C., preferably from 160° to 270° C. The reaction pressure may range from 0.1 to 300 $kg/cm^2$. The LHSV preferably ranges from 0.5 to 5 $Hr^{-1}$ in terms of production or reaction efficiency, though it may be optionally selected depending on the reaction conditions.

To further illustrate the present invention in greater detail, the following Examples will be given. It is to be understood here, however, that the present invention is never restricted thereto.

PREPARATION EXAMPLE I (Preparation of catalyst A)

To a 10 l separable flask provided with a stirrer and a thermometer, 3,500 g of ion-exchanged water, 790 g of nickel nitrate hexahydride and 34.5 g of copper nitrate trihydride were introduced and dissolved by heating to 60° C. Next, 169 g of zeolite (Molecular Sieve 13X) was added thereto as a carrier component and the mixture was heated to 90° C. A 10% aqueous solution of sodium carbonate was added dropwise thereto and thus a slurry (pH 8) was obtained.

The precipitate thus formed was filtered, washed with water, dried and baked at 600° C. for 1 hour. Thus a nickel/copper composite oxide containing zeolite was obtained. As the result of elemental analysis, the obtained oxide had the following composition.

NiO:CuO:zeolite=53%:3%:44%.

(Cu/Ni atomic ratio=0.05)

PREPARATION EXAMPLES II to V (Preparation of Catalysts B to E)

In accordance with the procedure of the above Preparation Example I, composite oxides (Catalysts B to D) listed in Table 1 were produced by varying the ratio of nickel nitrate hexahydride to copper nitrate trihydride. For comparison, another composite oxide (Catalyst E) was prepared by using nickel nitrate hexahydride and the carrier, without adding any copper nitrate trihydride.

TABLE 1

| | Cu/Ni Atomic Ratio | Composition of Composite Oxide | | |
| --- | --- | --- | --- | --- |
| | | NiO (%) | CuO (%) | Zeolite (%) |
| Catalyst B | 0.11 | 50 | 6 | 44 |
| Catalyst C | 0.41 | 39 | 17 | 44 |
| Catalyst D | 3.80 | 11 | 45 | 44 |
| Catalyst E | 0 | 56 | 0 | 44 |

EXAMPLES 1 TO 4 AND COMPARATIVE EXAMPLE 1

(Desulfurization)

The desulfurizing performances of Catalysts A to E were evaluated under the conditions as specified below by using palm kernel fatty acid methyl esters of a sulfur content of 3.0 ppm.

Evaluation of desulfurizing performance:

Each catalyst was extrusion-molded by using bentonite to give noodles of 5 mm in length and 2 mm in diameter. 15 g of the molded catalyst thus obtained and 200 g of lauryl alcohol were fed into an autoclave type basket reactor and activated by reducing under a hydrogen gas stream at a hydrogen pressure of 230 kg/cm$^2$ (gauge pressure) at 270° C. for 4 hours.

After the completion of the reduction, the lauryl alcohol was replaced with 200 g of palm kernel fatty acid methyl esters (sulfur content: 3.0 ppm; AV: 0.24 (KOH mg/g) and the reaction was performed under a hydrogen gas stream at a hydrogen pressure of 230 kg/cm$^2$ (gauge pressure) at 200° C. with stirring at 900 rpm for 4 hours. The sulfur content was measured with a Dohrmann type Low-Concentration Sulfur Meter system 701 (product of Rosemount Analytic Inc.) and the acid value was also measured.

Table 2 summarized the results.

EXAMPLE 5 AND COMPARATIVE EXAMPLE 2

(Desulfurization)

Purified palm kernel oil (AV: 0.07 (KOH mg/g) of a sulfur content of 4.0 ppm was desulfurized by the same method as described in Example 1 with the use of Catalysts C and E. Table 2 shows the results.

TABLE 2

| | Catalyst | Cu/Ni Atomic Ratio | Composition of Oxide | | | Evaluation | |
|---|---|---|---|---|---|---|---|
| | | | NiO (%) | CuO (%) | Zeolite (%) | Acid Value (KOH mg/g) | Residual Sulfur Content (ppm) |
| Example 1 | A | 0.05 | 53 | 3 | 44 | 1.2 | 0.30 |
| Example 2 | B | 0.11 | 50 | 6 | 44 | 0.93 | 0.30 |
| Example 3 | C | 0.41 | 39 | 17 | 44 | 0.28 | 0.30 |
| Example 4 | D | 3.80 | 11 | 45 | 44 | 0.26 | 0.52 |
| Comparative Example 1 | E | 0 | 56 | 0 | 44 | 1.8 | 0.52 |
| Example 5 | C | 0.41 | 39 | 17 | 44 | 0.30 | 0.35 |
| Comparative Example 2 | E | 0 | 56 | 0 | 44 | 1.9 | 0.57 |

EXAMPLE 6

(Production of Alcohol)

The fatty acid methyl ester obtained in the above Examples 1 to 4 and undesulfurized palm kernel fatty acid methyl ester were used as starting oils for reduction.

Table 3 shows the results of the evaluation of the catalyst life of the catalyst for ester reduction effected by using these starting oils.

The catalyst for ester reduction used herein is a copper-zinc catalyst carried on titanium (CuO:ZnO:TiO$_2$=47.5%:2.5%:50.0%) disclosed in JP-A-1-305042 (the term "JP-A" as used herein means an "unexamined published Japanese patent application) (corresponding to U.S. Pat. No. 4,918,248). (Evaluation of Activity Life of Catalyst for Ester Reduction) In a 0.5 l-volume autoclave equipped with a rotary stirrer, were charged 150 g of each of the starting oils and 3.75 g of the catalyst for ester reduction. The catalyst was activated in a hydrogen flow at a pressure of 10 kg/cm$^2$ and at a temperature of 200° C. for 2 hours. After evaluating the temperature to 230° C. and the hydrogen pressure to 120 kg/cm$^2$, the reaction was started at a stirring rate of 800 rpm and at a hydrogen flow rate of 5 l/min. The reaction system was sampled appropriately in the course of the reaction and analyzed to obtain the conversion ratio of the starting oil whereby the catalyst activity was obtained. The reaction was adjusted as a first-order reaction with respect to the oil concentration and the rate constant per gram of the catalyst before activation was taken as a criterion of the catalyst activity.

After the completion of the reaction, the catalyst was separated from the alcohol thus produced by filtration and reused in the next reaction. This procedure was replaced 10 times under the same conditions and thus the rated constant was determined per reaction. A reduction of activity per reaction was calculated according to the following equation.

$$\text{Activity Reduction} \atop (\% \text{ per times}) = \frac{K_1 - K_{10}}{K_1} \times 100 \div (\text{time of use})$$

where $K_1$ is a rate constant at the first time and $K_{10}$ is a rate constant at the tenth time.

In every experiment, the plots of rate constant against number of times of catalyst recovery revealed good linearity.

TABLE 3

| Starting Oil | Acid Value (KOH mg/g) | Sulfur Content (ppm) | Activity Reduction (%/times) |
|---|---|---|---|
| Example 1 | 1.2 | 0.30 | 0.80 |
| Example 2 | 0.93 | 0.30 | 0.75 |
| Example 3 | 0.28 | 0.30 | 0.70 |
| Example 4 | 0.26 | 0.52 | 0.82 |
| Undesulfurized Palm Kernel Fatty Acid Methyl Ester | 0.24 | 3.00 | 6.75 |

As the above results show, the activity reductions obtained by using the starting oils whose sulfur content had been reduced to 0.6 ppm or less in the desulfurization process of the present invention (starting fatty acid methyl esters obtained in Examples 1, 2, 3 and 4) are smaller than that of the undesulfurized palm kernel fatty acid methyl ester.

Thus it is obvious that the activity life of the catalyst in a reaction using the starting oil desulfurized in the present process is equal or longer than that using the undesulfurized oil.

While the invention has been described in detail and with reference to specific embodiments thereof, it will be apparent to one skilled in the art that various changes and modifications can be made therein without departing form the spirit and scope thereof.

What is claimed is:

1. A process for producing desulfurized fats and oils or fatty acid esters which comprises contacting fats and oils or fatty acid esters with a catalyst represented by the following formula (I) under a hydrogen atmosphere or a mixture of hydrogen with an inert gas:

$$Ni.Cu_xO_y \quad (I)$$

wherein x represents an atomic ratio of Cu determined by referring Ni a 1 and a value of from 0.02 to 8; and y is an atomic ratio of oxygen satisfying the valence requirements of Ni and Cu.

2. A process of claim 1, wherein said process is performed so as to give fats and oils or fatty acid esters of an acid value of 2 in terms of KOH mg/g or below and a sulfur content of 0.6 ppm or less.

3. A process of claim 1, wherein said fats and oils or fatty acid esters are contacted with said catalyst of formula (I) in a continuous fixed bed reaction system.

4. A process for producing alcohols which comprises the steps of:

(1) contacting fats and oils or fatty acid esters with a catalyst represented by the following formula (I) under a hydrogen atmosphere or a mixture of hydrogen and an inert gas:

$$Ni.Cu_xO_y \quad (I)$$

wherein x represents an atomic ratio of Cu determined by referring Ni as 1 and a value of from 0.02 to 8; and y is an atomic ratio of oxygen satisfying the valence requirements of Ni and Cu; and (2) catalytically reducing the desulfurized fats and oils or fatty acid esters obtained in said step (1) with hydrogen in the presence of a catalyst for ester reduction.

* * * * *